US006477891B2

(12) United States Patent
Ehwald et al.

(10) Patent No.: US 6,477,891 B2
(45) Date of Patent: Nov. 12, 2002

(54) PROCESS FOR AFFINITY VISCOSIMETRY AND VISCOSIMETRIC AFFINITY SENSOR

(75) Inventors: Rudolf Ehwald, Berlin; Karl-Ernst Ehwald, Frankfurt; Andreas Thomas, Pirna; Uwe Beyer, Hohenstein-Ernsthal, all of (DE)

(73) Assignee: Disetronic Licensing, AG, Burgdorf (CH)

( * ) Notice: Subject to any disclaimer, the term of this patent is extended or adjusted under 35 U.S.C. 154(b) by 0 days.

(21) Appl. No.: 09/897,357

(22) Filed: Jul. 2, 2001

(65) Prior Publication Data

US 2001/0035047 A1 Nov. 1, 2001

Related U.S. Application Data

(63) Continuation of application No. 09/416,839, filed on Oct. 12, 1999, now Pat. No. 6,267,002.

(51) Int. Cl.[7] ............... G01N 30/00; G01N 11/04; G01D 9/42
(52) U.S. Cl. ............... 73/54.01; 73/64.55; 73/54.02; 73/54.04; 73/64.56
(58) Field of Search ............... 73/54.01, 54.02, 73/54.04, 64.56

(56) References Cited

U.S. PATENT DOCUMENTS

| 3,677,069 A | 7/1972 | Rubin et al. ............... 73/56 |
| 4,454,751 A | 6/1984 | Matta et al. ............... 73/56 |
| 4,541,270 A | 9/1985 | Hanslik ............... 73/56 |
| 4,615,210 A | 10/1986 | Wright ............... 73/55 |
| 4,726,219 A | 2/1988 | Pearson et al. ............... 79/56 |
| 4,750,351 A | 6/1988 | Ball ............... 73/56 |
| 4,952,560 A | 8/1990 | Kigasawa et al. ............... 514/2 |
| 4,972,701 A | 11/1990 | Yau ............... 73/61.1 |
| 5,277,058 A | 1/1994 | Kalyon ............... 73/54.11 |
| 5,372,034 A | * 12/1994 | Burke ............... 73/54.11 |
| 5,542,289 A | 8/1996 | Hool et al. ............... 73/64.52 |
| 5,756,883 A | 5/1998 | Forbes ............... 73/54.05 |
| 5,847,268 A | 12/1998 | Ball ............... 73/54.09 |
| 6,261,244 B1 | * 7/2001 | Kensey et al. ............... 600/573 |
| 6,267,002 B1 | * 7/2001 | Ehwald et al. ............... 73/54.01 |

FOREIGN PATENT DOCUMENTS

| DE | 42 03 466 | 2/1992 |
| DE | 44 46 695 | 12/1994 |
| DE | 195 01 159 | 1/1995 |

OTHER PUBLICATIONS

Ballerstadt, R. et al. "Viscosimetric Affinity Assay", *Analytical Biochemistry* 234, vol. 0040, pp. 1–8 (1996).
Ballerstadt, R. et al. "Suitability of aqueous dispersions of dextran and Concanavalin A for glucose sensing in different variants of the affinity sensor", *Biosensors & Bioelectronics* 9 pp. 557–567 (1994).

* cited by examiner

*Primary Examiner*—Hezron Williams
*Assistant Examiner*—David J. Wiggins
(74) *Attorney, Agent, or Firm*—Dorsey & Whitney LLP

(57) ABSTRACT

The invention concerns a process for affinity viscosimetry and a viscosimetric affinity sensor on the basis of sensitive liquids with analyte-dependent viscosity which are localized within a perfusable dialysis chamber and contain colloidal constituents which are cross-linked by affinity bonds. The viscosimetric affinity sensor according to this invention is characterized by the spatial or temporal separation of analyte diffusion from the measurement of the flow resistance for such sensitive liquid flowing through a capillary, needle-like body or other liquid conductor, which integrated combination of a dialysis chamber with viscosimeter enables a researcher to make measurements under lab conditions that provide spatial separation of the dialysis process from the rheological analysis, as done under test conditions where the maximum shear rate of sensitive liquid in the viscosity sensor is at least twice that shear rate of sensitive liquid experienced in the dialysis chamber. An important advantage of the invention consists in small volume-displacement and negligible structural change within the matrix or organ of living tissue to be investigated.

8 Claims, 2 Drawing Sheets

PROCESS FOR AFFINITY VISCOSIMETRY AND VISCOSIMETRIC AFFINITY SENSOR

This application is a Continuation of U.S. patent application Ser. No. 09/416,839, filed on Oct. 12, 1999, now issued as U.S. Pat. No. 6,267,002, issued on Jul. 31, 2001, which is herein incorporated by reference.

CROSS-REFERENCE TO RELATED APPLICATIONS

DE 1 95 01 159 A1
DE 44 40 095 A1
DE 42 03 466 A1

STATEMENT REGARDING FEDERALLY SPORNSORED RESEARCH OR DEVELOPMENT

Not applicable

REFERENCE TO A MICROFICHE APPENDIX

Not applicable

BACKGROUND OF THE INVENTION

The invention relates to the technical field of affinity assays and affinity sensors in general and of the viscosimetric principle of determination of affinity bonds in special.

BRIEF SUMMARY OF THE INVENTION

The invention makes available a process of affinity viscosimetry and a viscosimetric affinity sensor suitable for measuring the concentration of low-molecular weight affinity ligands, e.g. sugars. The general idea of the invention consists in the measurement of the analyte-sensitive flow resistance of the sensitive liquid at a high shear rate. The shear rate at viscosity measurement is at least twice the shear rate at the dialysis process. The temporal and/or spatial separation of the dialysis process from the rheological analysis enables several advantages, especially miniaturization of the implantable part of the sensor and compensation of temperature effects.

DETAILED DESCRIPTION OF THE INVENTION

Figure 1:
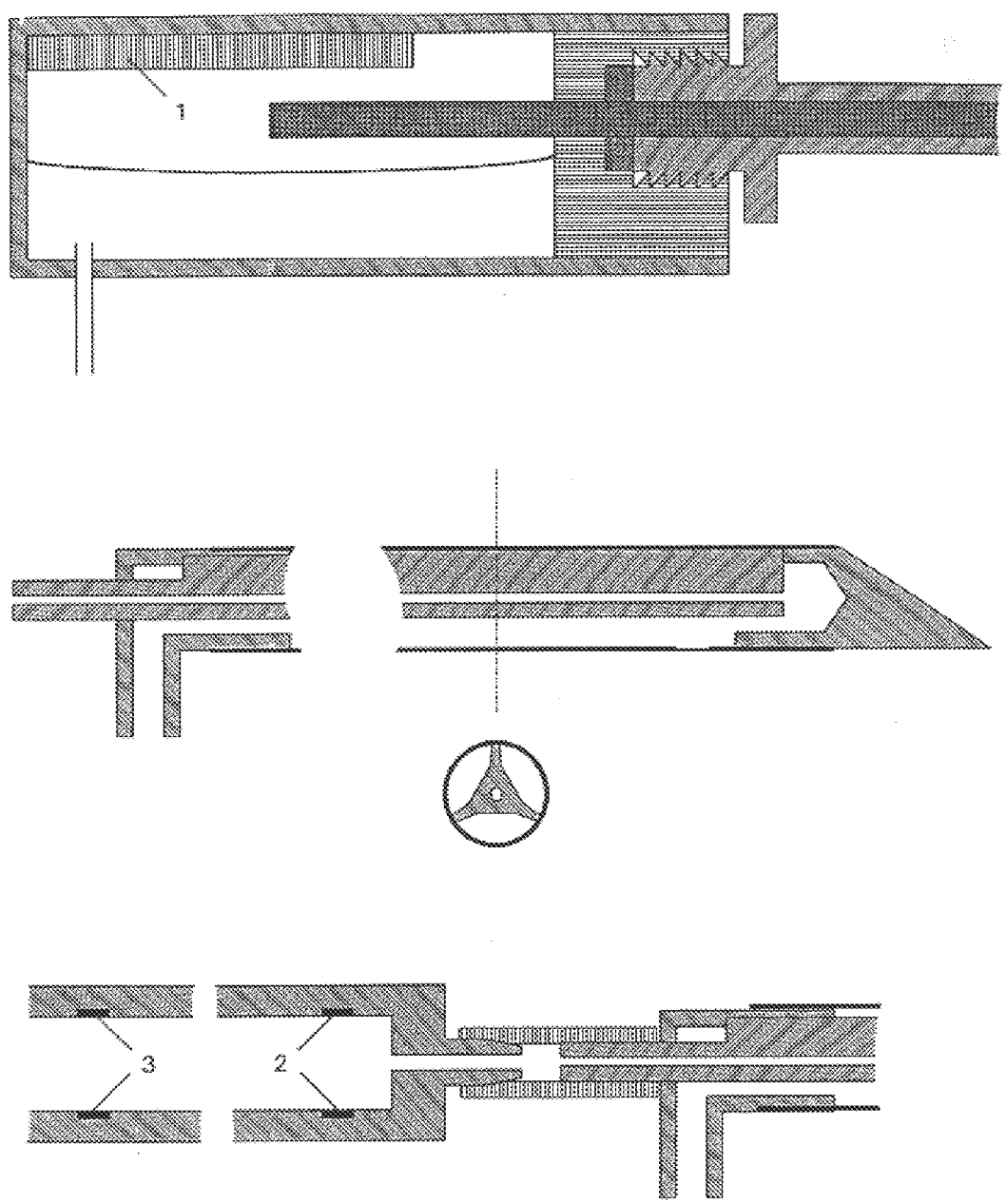
FIG. 1. Parts of the affinity sensor. Top: Bowden cable pump with pressure sensor (1), middle: implantable sensor part with central measuring capillary and surrounding dialysis chambers, bottom: electrode chamber with electrode pairs (2) and (3) connected to the implantable sensor part.

Viscosimetric affinity assays and related affinity sensors use the finding that a concentrated solution of a hydrocolloid and a di- or polyvalent affinity receptor, e.g. a lectin or antibody, has an analyte-dependent viscosity, if the following conditions hold: (1) the hydrocolloid exposes a structure that is similar to the analyte structure and forms affinity bonds to the affinity receptor in the aqueous solution, (2) the concentration of the hydrocolloid is above the critical concentration for partial overlapping of the macromolecules to a network solution (Ehwald, R., Ballerstädt, R., Dautzenberg, H.: Anal. Bioch. 234, 1–8, 1996).

Known viscosimetric affinity sensors measure the convective resistance of the sensitive liquid containing the mentioned components within a hollow fiber. A known technical concept of the viscosimetric affinity sensor consists in the analysis of oscillating liquid movement in open or closed liquid-conductors (Ballerstädt R. Ehwald, R: Biosensors & Biolectronics 9, 557–567 1994, Ehwald, R., OS DE 1950159 A1, 1996). In these sensors the hollow fiber is part of a liquid-conductor which may contain other fluids such as air or silicon oil which are used for transduction of the force to the sensitive liquid or the measurement of the flow velocity. The dimensions of the liquid-conductor are such that the flow resistance for the mentioned additional fluid (gas or low-viscosity oil) is small in comparison to the flow resistance of the sensitive liquid within the dialysis hollow fiber. This concept requires a device for restriction of the menisci within a certain oscillation region of the liquid-conductor.

For important application fields of biosensors it is desirable to minimize the volume displacement of the matrix by the sensor as well as the change of the matrix structure due to the introduction of the sensor into the object of investigation, e.g. the tissue of a living organism. Only the dialysis chamber, e.g. a dialysis hollow fiber, must have contact with the matrix. The integration of the dialysis chamber within a closed-flow conductor for the liquid which comprises a miniaturized pump and coupling fluid (Ehwald, R., OS DE 1950159 A1, 1996) is not favourable for space restriction of those sensor parts which are in contact with the matrix. The use of flexible tubings between the pump and the dialysis chamber for separating the dialysis chamber from the pump is not compatible with a defined mid point position of the oscillating menisci. There are interfering volume changes of the oscillating sensitive liquid at prolonged measuring periods, when the oscillating system is open to the atmosphere (Ballerstädt, R, Ehwald R: Biosensors & Bioelectronics 9, 557–567, 1994).

The task of the invention is to make available a process of affinity viscosimetry and a viscosimeteric affinity sensor, which are suitable for measuring time courses of the analyte concentration reproducibly. The parts of the sensor which have to be in contact with the matrix living tissue to be investigated should be of such kind that they can be replaced and introduced into a living tissue with little damage and structural change. The technical solution of the mentioned task is a process of affinity viscosimetry and an affinity sensor according to the claims.

The invention is founded on the combination of unexpected properties of the sensitive liquids with new principles of sensor construction.

Previous concepts of the viscosimetric affinity sensors are based on the well-known experience, that colloidal aggregate structures with reversible macromolecular association are sensitive to shear forces Their rheology is usually investigated at low shear rates (compare W. M. Kulicke, ed., Fließverhalten von Stoffen and Stoffgemischen, Hüthig & Wepf-Verl. Basel, Heidelberg, New York 1986, pp. 29–31, 52–97, 88–94, 210–221). Therefore, previously mentioned affinity sensors were constructed in such a way, that an oscillating liquid flow of low amplitude and frequency is realized within the dialysis hollow fiber.

Unexpectedly, it has been found that the sensitive liquids which are liquid polymer networks structurized by affinitycross links between dextran and Concanavalin A, respond to changes of the analyte concentration (glucose) more sensitively and reproducibly at high shear rates (5 to 1000 s$^{-1}$) than at lower ones. At low shear rate there is an unexpected dependence of the viscosity on the time and the previous shear treatment. The analysis of rheologic peculiarities of the sensitive liquids shows surprisingly that the viscosity of the sensitive liquids depends reproducibly on the free ligand concentration at sufficiently strong shear fields only. This enables the application of high shear rates and thereby allows the separation of dialysis and viscosity measurement, either in spatial or temporal respect. The diffusion of the analyte into the sensitive liquid can occur before the viscosity measurement when the sensitive liquid is not flowing at all or is streaming at low velocity and shear rate. Since the shear rate at viscosity measurement can be high, there is only a short time necessary for the measurement of the viscosity subsequent to dialysis, and this measurement can be done in a separate narrow measuring chamber.

In the claimed viscosimetric affinity sensor the dimensions of the pressure source, the dialysis chamber and eventually of the measuring chamber as well as the temporal regime of pumping are such that the shear rate at the viscosity measurement is significantly (at least two times) higher than the shear rate occurring in the dialysis chamber at the diffusional equilibration of the analyte.

Due to the claimed temporal and eventually spatial separation of dialysis and viscosity measurement the sensor can operate permanently without the need that the sensitive liquid is restricted to the dialysis fiber. The application of high shear rates facilitates the construction of an exchangable and implantable sensor part, the surface of which is a dialysis membrane. This part, the dialysis chamber can be integrated within a needle-like body, separately from the further parts of the liquid-conductor, and this body can be easily introduced into a living tissue. The combination of the mentioned properties allows of the construction of a device wherein the implantable sensor part is exchangeable and connected to the pump by flexible tubings or other flexible systems of mechanical force transduction.

In one variant of the claimed sensor the analyte containing sensitive liquid obtained in the dialysis chamber by diffusional equilibration with the matrix can be sucked totally or partly through a measuring chamber. It is replaced in this process by a gas or a liquid fluid and the flow resistance of the measuring chamber is such that it dominates the whole flow resistance of this process.

If the flow resistance is controlled by a measuring chamber with comparatively small volume, the viscosity measurement can be carried out in a continuous flow with constant rate. It is essential in this case that the residence time of the flowing sensitive liquid within the dialysis chamber is sufficient for diffusional equilibration of the analyte between the external matrix and the lumen of the dialysis chamber.

Due to the applicability of high shear rates, the residence time of the sensitive liquid within the dialysis chamber can be kept small during the measuring of the flow resistance. Therefore, there is no significant retardation of the signal registration at discontinuous flow through the dialysis chamber. Alternating periods of dialysis (non or slow movement) and short periods of viscosity measurement (fast flow, high shear rate) can be applied to measure analyte-concentrations. In this case, a special measuring chamber is not necessary for the desired separation between dialysis and viscosity measurement, and a thin hollow fibre may be used as a dialysis chamber and the dominating flow resistance as well.

The invention allows for several advantageous technical variants. The sensitive liquid can be pumped from a storage container through a dialysis chamber and a chamber for measuring the viscosity (flow resistance) into a final container, whereby the equilibration of the analyte in the dialysis chamber is guaranteed by the choice of an appropriate flow rate. The analyte-dependent flow resistance can be registered by different well-known principles, e.g. measuring the electrical current necessary to drive the pump with constant flow rate, by means of the pressure difference by a suitable pressure sensor, or by measuring the velocity of liquid movement at defined pressure. Both oscillating and stationary flow of the liquid are applicable.

To reduce the flow resistance in the tubings outside the dialysis and measuring chambers, a gas, a gas mixture or a nonaqueous transport fluid of low viscosity can be introduced into the liquid-conductor. In this case two steps can be involved in the measuring process: 1. equilibration of the sensitive liquid in the dialysis chamber with the matrix to be investigated, 2. introduction of the low-viscosity fluid into the liquid-conductor close to the dialysis chamber, thereby moving the equilibrated sensitive liquid from the dialysis chamber through the measuring chamber with sufficiently high shear rate. The second step allows of the measurement of the analyte-dependent viscosity.

The dialysis chamber can be constructed in such a way that it consists of a space between a solid body and the dialysis membrane. The dialysis chamber can be made from segments of a commercial dialysis hollow fiber that surrounds a thin capillary as usual in microdialysis. The enclosed capillary can be used as a measuring chamber.

When the flow resistance is measured by the electrical current or the electrical power at constant flow rate the pump is constructed and controlled in order to create a flow rate that is independent of the flow resistance, e.g. a pump with a piston that is combined with a threaded rod driven with high step-down ratio by an electromotor. Possible variants of the sensor have a pump that sucks at one face of the liquid-conductor and pumps at the other face. Besides the mentioned types of pumps others, e.g. dielectric or magnetic ones, gas pumps, or pumps driven by the force of a spring can be applied.

The flow resistance of the flowing sensitive liquid in the measuring chamber can be determined by measuring the time necessary for the movement of a defined volume. The latter measuring principle can be realized by measuring the time for the movement of a gas-liquid meniscus between two electrical or optical marks. If the direction of the pressure difference is altered at reaching the mark by a suitable electronic control system, the movement of the meniscus can be restricted to a segment of the liquid-conductor between electrical or optical marks. In this case, an oscillating movement of a part of the sensitive liquid from the dialysis chamber(s) into and through the measuring chamber can be obtained. At a defined pressure difference, the duration of the oscillation period is proportional to the flow resistance of the sensitive liquid in the measuring chamber.

As high shear forces are compatible with the principle of the viscosimetric affinity sensor, the measuring chamber can be kept narrow and short. Therefore, it is possible to keep the flowing volume very small and to choose a short measuring chamber with high resistance for viscous flow. This enables a special variant of the sensor, where the dialysis fiber is connected to a blind end of the liquid-conductor at one face and with the measuring chamber and pump at the other face. When the volume flow resistance of the dialysis membrane is comparable or higher than the flow resistance of the measuring chamber, it is necessary to ensure a sufficiently high elastical volume capacity of the blind ending part of the liquid-conductor. A sufficient volume capacity of the blind ending part can ensure that the flow is controlled by the viscous resistance in the measuring chamber.

The invention will be specified by the following examples

A. The sensor contains the following parts: an electromotor with threaded rod and Bowden cable, a pumping vessel containing the sensitive liquid and a pressure sensor (FIG. 1, above), a dialysis needle (FIG. 1, middle part) and a tank for collecting consumed sensitive liquid. The electromotor drives a threaded rod with high step-down ratio and thereby moves the wire of the Bowden cable into the pumping vessel or out of it. The pumping vessel consists of ceramics or another very stiff material and is separated into two chambers by a highly flexible membrane. One chamber contains a pressure sensor (1) and is filled with gas-free silicon oil. This chamber is connected with the Bowden cable. The other chamber is filled with the sensitive liquid (e.g. a solution of 70 mg/ml Dextran T2000 and 10 mg/ml Concanavalin A) and is connected with the dialysis needle by a ca. 10 mm long polypropylene tubing. The sensitive liquid in the pumping chamber may contain the analyte (e.g. glucose) in a concentration which is typical for the investigated matrix. The dialysis needle (FIG. 1, middle part) contains, as usual for microdialysis, a capillary that is enclosed within a dialysis chamber or dialysis chambers. The cross-sectional area of the dialysis chamber(s) is significantly larger than that of the capillary lumen. The dialysis chamber is connected with the collecting tank for the sensitive liquid by short tubing. The collecting vessel is a short polypropylene tube containing self-sucking porous material, e.g. cotton. It is open to the atmosphere. The dialysis needle has a higher flow resistance than the tubings.

This variant of the sensor allows of the following measuring process. In the first step the metal wire of the Bowden cable is pushed into the silicon oil of the pumping vessel rapidly and as far as necessary to allow a complete replacement of the sensitive liquid in the dialysis chamber. The speed of this step is such that a well measurable pressure increase is measured by the pressure sensor. The time course of the pressure signal during the pumping process and/or its relaxation is analyzed electronically. After a dialysis time of ca. 2 min the metal wire is redrawn for a short extent. Preferably, the extent of this backward volume displacement is smaller than that at the inward displacement. By comparing the pressure signals at inflow into the dialysis chamber (known analyte concentration in the measuring capillary) and backflow out of the dialysis chamber (analyte concentration in the measuring chamber equal to that of the matrix), it is possible to determine the analyte concentration in the matrix from a calibration curve. The reference to a prefixed value of the analyte concentration renders temperature compensation unnecessary. As inward pumping strokes induce a larger flow than backward strokes, the dialysis chamber is filled with new sensitive liquid of standard glucose concentration at the beginning of each measuring cycle.

B. The liquid-conductor of the sensor consists of the following components in series: a pump and a dialysis needle as in A, an electrode chamber (FIG. 1, bottom), a collecting tank for the consumed sensitive liquid, a low-pressure chamber, and a gas pump. The electrode chamber is localized between the dialysis chamber and the collecting tank for the consumed sensitive liquid, the measuring capillary between the dialysis chamber and the pump. One polypropylene tube connects the measuring capillary with the pumping vessel for the sensitive liquid, another one connects the electrode chamber with the collecting tank for consumed sensitive liquid. The collecting tank and the pumping vessel with the Bowden cable are similar as explained in example A; however a pressure sensor is not necessarily involved. There are valves which can be used to connect the collecting tank either with the low-pressure reservoir or the atmosphere. The low-pressure reservoir is kept at a defined gas pressure below the atmosphere value by means of the gas pump. Close to the measuring capillary the polypropylene tube connecting the pumping vessel with the measuring chamber in the dialysis needle is narrow (inner diameter ca. 200 $\mu$m). At this place the tubing wall is perforated by narrow pores. The electrode chamber has a diameter of ca. 200 $\mu$m. Its inner wall contains two pairs of electrically insulated electrodes arranged to be mutually separated in a defined distance. The capacity measured at these electrode pairs responds to movement of the meniscus through the electrode chamber.

This variant of the sensor allows of the following measuring process: The collecting tank is set to atmospheric pressure. A small amount of the sensitive liquid will be driven by the pump through the dialysis needle and the electrode chamber into the collecting tank. Subsequently the liquid column is moved slowly backward until the meniscus reaches the first electrode pair (2) of the electrode vessel. The obtained capacitance signal is used to interrupt the pump activity. After a dialysis time of about 3 min the valve to the atmosphere is closed and the collecting vessel set to defined low-pressure by opening the valve to the low-pressure chamber. This way the liquid column is set under tension and air enters into the sensitive liquid at the porous site of the tubing wall. Subsequently a small amount of the sensitive liquid is separated from its reservoir in the pumping vessel and moves through the dialysis needle towards the collecting tank. The time between the opening of the valve to the low-pressure reservoir and the movement of the meniscus through the site of the second electrode pair is a measure for the analyte-dependent viscosity of the sensitive liquid after the dialysis. The whole separated portion of the sensitive liquid is driven into the collecting vessel. After a time sufficient for this process, the next measuring cycle is prepared. For this purpose the collecting vessel is set to atmosphere pressure and the liquid conductor is refilled by the Bowden cable pump.

C. The fluid conductor of the sensor contains the following parts in series: a pumping vessel for the sensitive liquid, a branched tubing, an electrode chamber, a dialysis needle and a collecting tank connected by valves with the atmosphere or a gas pressure source consisting of a chamber with reduced or increased gas pressure, and a gas pump.

The pumping vessel for the sensitive liquid, the electrode chamber, the dialysis needle and the collecting vessel are constructed in the same kind as described in examples A and B. The dialysis needle is connected with the polypropylene tubings in such a way that the dialysis chamber is next to the collecting tank and the electrode chamber next to the measuring capillary. In a short distance to the electrode chamber there is a short branching of the polypropylene tubing with a valve, by means of which the liquid column can be set under atmospheric pressure. The electrode space is situated between the measuring capillary and the branching. The volume between the electrodes is comparable to the volume of the dialysis chamber. The dialysis chamber is connected by short distance with the collecting vessel. The polypropylene tubing between the gas-pressure source and the collecting vessel contains valves by which it can be connected either with the pressure source or the atmosphere.

This variant of the sensor allows of the following measuring process: The pumping device drives a small amount of the sensitive liquid, about twice the volume of the dialysis chamber, with low rate into the collecting tank, whereby the gas-entry valve at the branching is closed and the tubing between collecting tank and the gas pressure source is at atmospheric pressure. Meanwhile the gas reservoir is set at a defined pressure below atmosphere by the use of a gas pump. Thereafter the gas entry valve at the branching and the valve between the gas pressure source and the colleting vessel are opened. Air enters into the tubing at the branch, and the menisus is driven through the electrode space towards the collecting tank. The time necessary for the movement of the meniscus between the electrode pairs is proportional to the flow resistance of the sensitive liquid in the measuring capillary before its equilibration with the matrix. When the meniscus has reached the electrode pair close to the measuring capillary, the obtained capacitance signal is used to set the liquid column to the atmospheric pressure, whereby the liquid column is stopped. During the dialysis time of ca. 2 min a defined over-pressure is created in the gas pressure chamber. Subsequently the gas pressure source is connected with the liquid column again, whereby the meniscus is driven back through the measuring capillary. Now the sensitive liquid flowing through the measuring capillary is modified by the analyte of the matrix. Preferably, in this arrangement the sensitive liquid in the reservoir of the pumping vessel contains the analyte in a defined reference concentration. The deviation from this concentration can be obtained by the ratio of the displacement times in both directions of liquid movement. As the ratio of the affinity-mediated viscosities at different analyte concentrations is little dependent on temperature, this variant of the affinity sensor gives accurate data even without thermostatting. Finally the valve at the branch is closed and the next measuring cycle prepared by pumping fresh sensitive solution towards the collecting tank.

Figure 2:
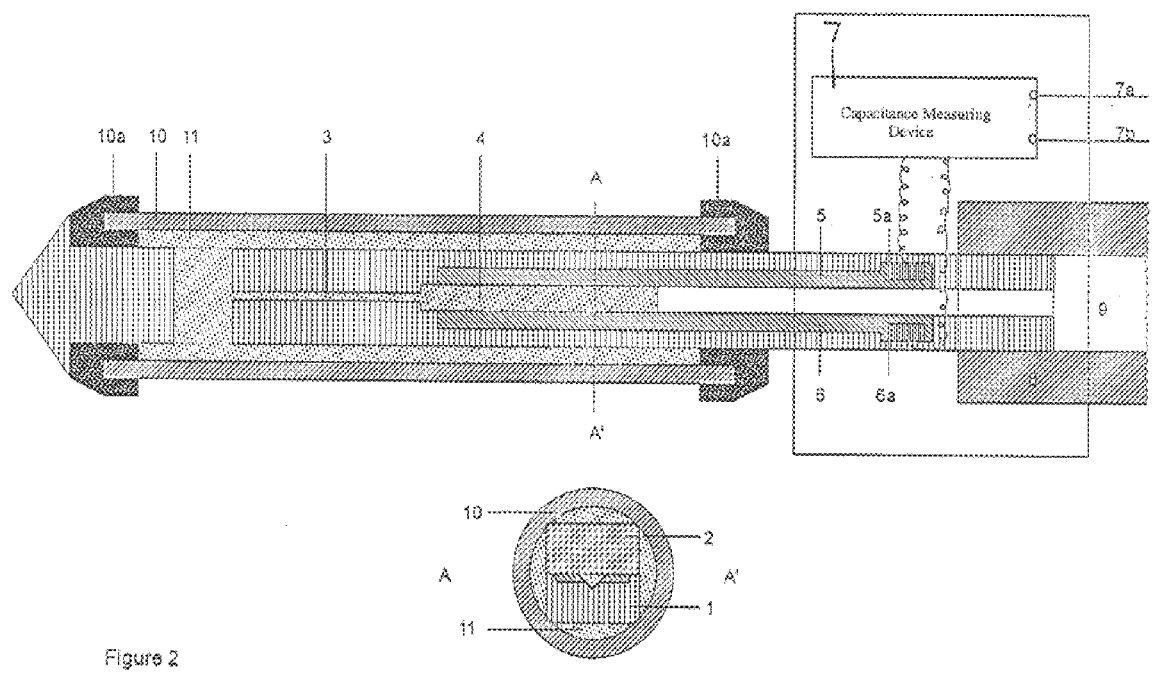
FIG. 2. Implantable sensor part made by silicon technology. The figure shows the silicon body (1), the glass cover (2), the measuring capillary (3), the electrode chamber (4), the p-conducting edges used as electrodes (5 and 6), their contacts (5a, 6a), the capacitance measuring device (7), the connections to the external data logger (7a and 7b), wall (8) and lumen (9) of the gas tubing, the hollow fiber segment (10), a glue connection (10a), the sensitive solution in the dialysis chamber (11).

D. The sensor needle (FIG. 2) is made by semiconductor technology: It contains a blind ending dialysis chamber realized by a hollow fiber segment (10), a measuring capillary (3) and a capacitance measuring chamber (4) with suitable electrodes (5). The n-conducting, ca. 200 µm thick, 0.5 mm wide, and 20 mm long silicon substrate (1) contains a V-edged three angular furrow (3, 4) and is bonded gas- and water-tight with a fitted covering plate consisting of boron silicon glass (2). A part of the furrow (at 4) is deeper than the other one (at 3). Both parts form, together with the covering plate, a capillary with a three angular cross-section. The inner wall of the capillary is completely covered with $SiO_2$ by thermic oxidation of the silicon substrate after the V-edging. The cross-sectional area of the capillary of the deeper furrow (4) is about 5 times larger than that of the flatter one (3). The edge of the deeper furrow is formed by p-conducting zones (5) and (6). The p-conducting zones are separated from each other by the furrow and the n-conducting silicon substrate and contain contacts (5a) and (6a), which are connected with a capacitance measuring device (7). The narrow furrow used as measuring capillary (3) is open by windows in the silicon body to the blind ending dialysis chamber (11). The dialysis chamber, the measuring capillary (3) and a part of the electrode chamber (4) are filled with the sensitive liquid. The dialysis fiber segment (10) is tightly glued with the needle body (10a). The electrode capillary (4) is connected by a thin gas tubing (8, 9) to a gas pump that is able to create pressure differences to the atmosphere (−0.09 to +0.3 MPa). The needle-like sensor such described can be fitted into a cannula and this way introduced into the matrix, e.g. a living tissue.

This variant of the sensor allows of the following measuring process: By application of a gas pressure of ca.+0.3 MPa the sensitive liquid is moved within some seconds (<10 s) from the electrode space into the dialysis chamber until the meniscus reaches the measuring capillary, whereby water is extruded through the hollow fiber membrane, and the dialysis chamber is elastically stretched. At emptying the electrode space, the capacitance between the contacts (5a) and (6a) is falling below an incipient value. This is the signal to change the pressure to a below-atmosphere value (ca. −0.08 MPa), whereby the electrode chamber is refilled. When the maximum capacitance is reached, the direction of the gas pressure is changed again and the electrode space is emptied speed or the frequency of filling the electrode chamber registrated by the change of the capacitance depends on the glucose concentration in the dialysis chamber. In order to prevent differences in the glucose concentration between measuring and dialysis chamber, a repeated filling and emptying of the measuring chamber is recommended.

What is claimed is:

1. A viscosimetric affinity sensor for measuring viscosity at high shear rates; comprising
   a liquid-conductor perfusable by a shear sensitive liquid;
   a dialysis chamber having a tubular lumen and dialysis membrane for performing a dialysis treatment during a dialysis process; and
   a measuring chamber for determining a flow resistance of said sensitive liquid passing therethru and a connected pumping device, whereby the flow resistance of the measuring chamber is such that a maximum shear rate in the sensitive liquid within said measuring chamber is more than twice the maximum shear rate occurring in the sensitive liquid during the dialysis process.

2. A viscosimetric affinity sensor according to claim 1, further comprising a needle-like body, wherein the dialysis chamber is part of the needle-like body.

3. A viscosimetric affinity sensor according to claim 1, wherein the liquid-conductor contains a pressure sensor.

4. A viscosimetric affinity sensor according to claim 1, further comprising a needle-like body, wherein the measuring chamber is situated within the needle-like body and the dialysis chamber is situated at its surface.

5. A viscoimetric affinity sensor according to claim 1, wherein the dialysis chamber includes an additional chamber.

6. A viscosimetric affinity sensor according to claim 5, wherein the additional chamber contains a set of one or more electrodes for determining location of an interface between a fluid and said sensitive liquid contained therein, by which a position of a meniscus between fluid and sensitive liquid can be followed.

7. A viscosimetric affinity sensor according to claim 1, wherein the sensor contains a valve or a valve-like device for allowing an interruption of a cohesion behavior within the sensitive liquid, whereby this valve or valve-like device is placed between the dialysis chamber and the measuring chamber or between the dialysis chamber and the pumping device.

8. A viscosimetric affinity sensor according to claim 1, wherein the lumen of the dialysis chamber further comprises a solid body and defines a space between the solid body and the dialysis membrane.

* * * * *